United States Patent [19]
He et al.

[11] Patent Number: 5,981,464
[45] Date of Patent: Nov. 9, 1999

[54] ADJUVANT COMPOSITION

[75] Inventors: Mengtao He, Wayne; Gregory McFann, East Rutherford; Terence Farrell, West New York, all of N.J.

[73] Assignee: Lever Brothers Company, Division of Conopco, Inc., New York, N.Y.

[21] Appl. No.: 09/012,989

[22] Filed: Jan. 26, 1998

[51] Int. Cl.$^6$ .............................. C11D 17/00; A61K 7/48
[52] U.S. Cl. .................. 510/451; 510/141; 510/447; 510/451; 510/463; 510/486
[58] Field of Search .......................... 424/59, 60, 195.1, 424/401; 510/141, 152, 153, 155, 451, 447, 463, 486

[56] References Cited

U.S. PATENT DOCUMENTS

| | | | |
|---|---|---|---|
| 4,551,332 | 11/1985 | Stillman | 424/195.1 |
| 4,664,914 | 5/1987 | Stillman | 424/195.1 |
| 5,154,849 | 10/1992 | Visscher et al. | |
| 5,510,050 | 4/1996 | Dunbar et al. | |
| 5,554,315 | 9/1996 | Tonomura et al. | |
| 5,817,609 | 10/1998 | He et al. | 510/133 |

FOREIGN PATENT DOCUMENTS

| | | |
|---|---|---|
| 0617955 | 10/1994 | European Pat. Off. |
| 1570142 | 6/1980 | United Kingdom |
| 92/13060 | 8/1992 | WIPO |

OTHER PUBLICATIONS

International Cosmetic Ingredient Dictionary, 1997 edition, CTFA Publication

*Primary Examiner*—Mark Kopec
*Assistant Examiner*—Gregory E. Webb
*Attorney, Agent, or Firm*—Ronald A. Koatz

[57] ABSTRACT

The present invention relates to novel chip compositions containing specific polyol ester as the major carrier for liquid skin benefit agents. Addition of specific polyol esters wherein the melting temperature and HLB are specifically defined has been found to remarkably enhance the oil/humectant structuring capability of a skin cleansing bar. Such a polyol ester also permits the liquid benefit agents to be released into a personal wash liquor and then to be delivered to skin via personal wash. In a second embodiment, the invention relates to a method for enhancing the bar's capability of including high levels of oil and/or humectant by applying the adjuvant technology. That is, by coextruding and stamping the mixture of chips containing skin benefit agents and base chips containing a surfactant system, high levels of oils and/or humectants can be incorporated into solid toilet bars by standard extrusion technology. In the third embodiment, skin mildness and especially skin moisturization are significantly enhanced by the detergent bar compositions comprising the combination of the specific polyol ester with oil and/or humectant.

34 Claims, 1 Drawing Sheet

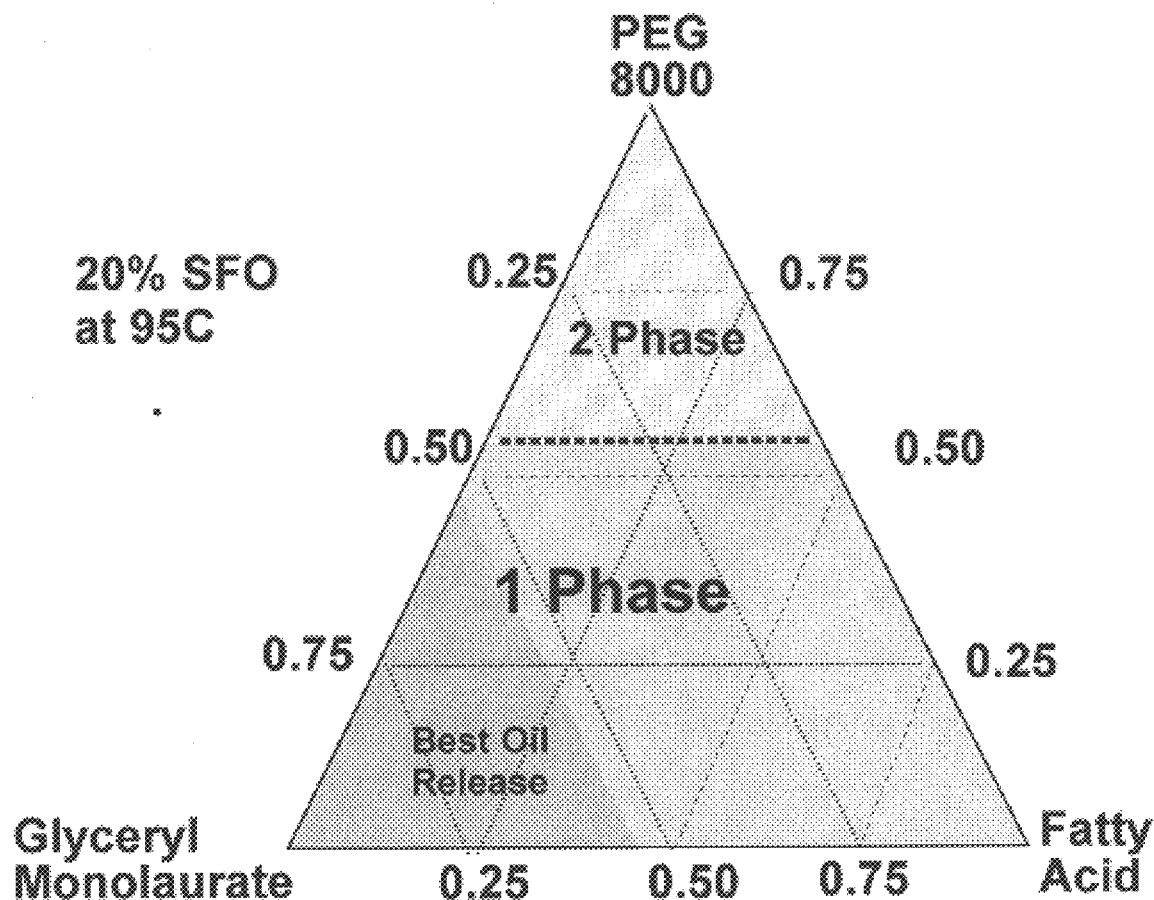

5,981,464

ADJUVANT COMPOSITION

FIELD OF THE INVENTION

The present invention relates to personal wash bar compositions, particularly compositions comprising (1) one or more surfactants, (2) one or more liquid emollient oils and/or humectants, and (3) a solid polyol ester with specifically defined HLB and melting temperature. In particular, the invention relates to chip compositions comprising emollient droplets entrapped and/or dissolved in a specific solid polyol ester as the thickened carrier. The emollient containing thickened carrier compositions are formed as separate chip/powder/granule compositions (referred herein as adjuvant chips) and are then mixed with "base" chips (comprising the surfactant system) prior to milling, extruding and stamping the bars. Through careful balancing of the polyol ester to oil and/or humectant ratio in the adjuvant chips, a novel approach of delivering mild, moisturizing ingredients to the skin via personal wash bar is developed. The invention relates to a method of making the additives. The invention further relates to a method of enhancing delivery of benefit agents from bars which method comprises mixing the base chips with the benefit agent containing adjuvant chips, milling, extruding and stamping.

BACKGROUND

It is technically difficult to include high levels (e.g., 10–20%) of liquid hydrophobic emollient oil (e.g., sunflower seed oil) and/or hydrophilic liquid humectant (e.g., glycerin) in the form of a solid personal washing bar and meanwhile maintain the bar mildness and benefit delivery to the human skin.

For example, high levels of humectants (e.g., glycerin, low MW polyalkylene glycol) can be trapped in a solid matrix of caboxylic fatty acid soap. However, it is known that carboxylic soap is harsh to skin especially when the soap concentration is high and when the soap is dissolved in the aqueous washing liquor through its own hydrophilic tendency or through the acts of cosurfactants in the bar.

On the other hand, non-soap synthetic bar formulations are primarily structured by either hydrophobic crystalline materials such as free fatty acid or paraffin wax or by hydrophilic crystalline materials such as polyalkylene glycol of high molecular weight (e.g., MW between 2000 and 20000).

Not to be bound by the theory, formulating high levels of emollient oil into the hydrophobic crystalline materials is believed to result in tightly binding the oil with the hydrophobic crystalline structurants. This contributes to the incapability of releasing the oil to water from the bar and may prevent delivering oil to skin via personal wash (see Example 1).

Including liquid oils and/or liquid humectants in bars structured by hydrophilic crystalline materials leads to another difficulty. That is, the oil and the humectant are not compatible with the hydrophilic structurants such as PEG 8000, and this incompatibility results in oil leakage and phase separation from the bulk portion of the bar solid (see Example 1).

Therefore, a novel mild bar structuring system is required to be able to satisfactorily structure the oil and/or the humectant in the bar solid while simultaneously permitting oil release from the bar to the aqueous liquid and then to the human skin via the route of personal wash.

Novel to the art, the applicants of the subject invention found a specific group of polyol esters (i.e., having specific ranges of HLB and specific melting temperature) are capable of both structuring a high level of hydrophobic emollient oils and/or humectants in solid form while still permitting the oil and humectants to be released from the solid into aqueous liquor to be delivered to the human skin through the route of personal wash. Balancing the ratio between polyol ester and oil/humectant are critical to achieve the desired oil structuring and oil releasing. The polyol ester solids containing high level of emollients/humectants can be processed into the form of soft solid chips, flakes or powders and then mixed with "base" chips (comprising the surfactant system) prior to milling, extruding and stamping the bars. This specific way of processing the bars is referred herein as the "adjuvant technology". Using the said specific polyol esters to incorporate high levels of emollients/humectants in the adjuvant chips that are then mixed with the base chips results in novel bar formulations, which are able to deliver high dosage of benefit agents to skin via personal wash and provide satisfactory bar user properties such as cream and/or lotion-like lather even in the presence of high oil levels. The presence of high levels of oil and/or humectant in bar made by said adjuvant technology also effectively reduces the skin irritation potential of surfactants.

The use of polyol esters in personal washing bars is not new.

European Patent Application EP 94105052.8 assigned to Kao Corp. (invented by M. Tonomura and T. Ohtomo), for example, teaches the use of monogyceridesto boost the lather of formulations comprising only nonionic surfactants. The application does not teach the use of the combination of specific solid monoglycerides and high level of liquid emollient oils/humectants to make bars, preferably pourable, cast melt bars, preferably comprising anionic surfactants and amphoteric surfactants. It does not teach the use of "adjuvant technology" to make high emollient/humectantcontaining bars in general. By contrast, the subject invention found that by using a specific polyol ester (e.g., specific range of HLB, polyol ester to oil/humectant ratio), high levels of emollient oil and/or humectants can be satisfactorily incorporated into adjuvant chips and then mixed with the "base chips" through the adjuvant technology.

An international application published under PCT WO 92/13060 to Procter & Gamble (authored by R. James) teaches the use of monoglycerides in general, PEG and fatty acid as binders for an extruded syndet bar formulation. The prior art, however, does not teach the use of a specific combination of specific monoglycerides (e.g., specific ranges of HLB) and PEG and fatty acid to incorporate high level of liquid emollients (e.g., vegetable oils)/liquid humectants (e.g., glycerin) to make a bar. The prior art also does not teach the specific bar formulation spaces to ensure that high levels of liquid oils and/or humectants can be structured in the solid bar matrixes and can be delivered to skin via personal wash. In contrast, the subject invention uses the adjuvant technology to prepare chips containing high levels of oils and/or humectants. By using a specific polyol ester (e.g., polyol esters with specific range of HLB, specific polyol ester to oil ratio, and specific polyol ester to other structurant (e.g., PEG and fatty acid) ratio), high levels of emollient oil and/or humectants can be satisfactorily incorporated into adjuvant chips and then into bars and can be delivered from the bars to skin under the personal wash condition.

U.S. Pat. No. 5,510,050 to J. Dunbar, P. Beerse, and E. Walker also teaches the use of monoglycerides in general as a non-preferred candidate for the plasticizers in an extruded cleansing bar containing liquid polyols (4–15%) and magnesium soap (4.5 to 50%). The preferred plasticizers are fatty acids, sodium soap, and paraffin wax (Column 5, line 22–24). The prior art, however, does not teach the use of a specific combination of specific monoglycerides (e.g., specific ranges of HLB) and other plasticizers to incorporate high level of liquid emollients (e.g., vegetable oils)/liquid humectants (e.g., glycerin) into a bar. The prior art also does not teach the specific bar formulation spaces to ensure that high levels of liquid oils and/or humectants can be structured in the solid bar matrixes and can be delivered to skin via personal wash. In fact, as found by the subject invention, the preferred plasticizers used in the prior art hinder the skin deposition of liquid oils from bars to skin. The prior art has to use magnesium soap as the key ingredient to aid processing (column 2, line 26). In contrast, the subject invention uses the adjuvant technology to prepare solid chips containing high levels of oils and/or humectants. By using a specific polyol ester (e.g., polyol esters with specific range of HLB, specific polyol ester to oil ratio, and specific polyol ester to other structurant (e.g., PEG and fatty acid) ratio), high levels of emollient oil and/or liquid humectants can be satisfactorily incorporated into chips and then into bars and can be delivered from the bars to skin under the personal wash condition. In the subject invention, carboxylic acid soap is not included in the chip composition and is an optional ingredient of the total bar composition.

A Great Britain Patent GB 1,570,142 assigned to GAF Corp. teaches the use of both hardened triglycerides and fatty alcohols as the plasticizers in an extruded syndet formulation. In contrast to the subject invention, the application does not teach the use of the combination of specific monoglycerides and high level of liquid emollient/humectants to make bars. It does not teach the use of adjuvant technology to make high emollient/humectant containing bars in general. By contrast, the subject invention found that by using a specific polyol ester (e.g., specific range of HLB, polyol ester to oil ratio, and polyol ester to other structurant ratio), high levels of emollient oil and humectants can be satisfactorily incorporated in the bar for the skin benefit through the adjuvant technology.

The art of using the adjuvant technology to incorporate emollients into bars is not new.

U.S. Pat. No. 5,154,849 to Visscher et al. teaches bar compositions containing a silicone skin mildness/moisturizing aid component. In one embodiment, the silicone component may be mixed with a carrier which is selected to facilitate incorporation of the silicone. At column 16, the reference describes that silicone is mixed into melted Carbowax (i.e., polyethylene glycol), that the mixture is cooled to form flakes, and that the flakes are preferably added to an amalgamator.

It is clear, however, that the Visscher et al. contemplates a silicone/carrier system different from the adjuvant chips of the subject invention. First, the Visscher patent does not teach selecting a carrier having specific HLB to both carry high levels of oils and permit oil release from the solid into water. For example, polyethylene glycol (HLB>18) is not miscible with most of hydrophobic oils such as silicone oil or vegetable oil at mixing temperatures (e.g., 70–120° C.), and upon cooling, oil tends to leak out of the PEG solid matrix. Therefore PEG has a poor oil-carrying capacity although it permits oil release from oil into water and then to skin via personal wash (see Example 1). On the other hand, fatty acid, ethers, alcohols or paraffin wax (HLB<2) have high oil carrying capability (Example 1); however, it is difficult to have oils released from those hydrophobic solids into water and then to skin at conditions relevant to personal wash. Novel to the art, subject invention found that specific solid polyol esters (i.e., specific HLB between 2.5 and 15) are capable of carrying high levels of oil/humectant and simultaneously providing oil release from the solid into water then to skin via personal wash.

U.S. Patent applications filed by Unilever (95-R385-EDG and 95-R385-B-EDG) use additional thickeners such as fumed silica or additional hydrophobically modified polyalkylene glycols or EO-PO copolymers to improve the oil-carrying capability of polyalkylene glycol in the adjuvant chips and to modify the dissolution speed of the adjuvant chips in water. Nevertheless, those applications use highly hydrophilic materials such as PEG and EO-PO (HLB>>15) and do not teach selecting a carrier having specific HLB (between 2.5 and 15, preferably between 2 and 8) to not only carry high levels of oils but also permit oil release from the solid into water. For example, polyethylene glycol (HLB>18) or hydrophobically modified PEG claimed (HLB>15) are not miscible with most of hydrophobic oils such as silicone oil or vegetable oil at mixing temperatures (e.g., 70–120° C.), and, upon cooling, oil tends to leak out of the solid matrix (see Example 1). Thus thickeners such as fumed silica have to be added to improve the adjuvant's oil-carrying capacity. Nevertheless, fumed silica is in the form of very fine powders (i.e., 7–30 millimicrons), which increase the processing difficulties and potentially increase the cost. By contrast, subject invention teach the use of specific solid polyol esters (i.e., specific HLB between 2.5 and 15) to carry high levels of oil/humectant and provide oil release from the solid into water then to skin via personal wash without or with a reduced level of thickeners such as fumed silica (e.g., 0–0.5%), which is advantageous because potentially processing can be simplified and cost can be reduced.

In summary, none of the references, alone or in combination teach that the use of specific polyol esters (e.g., having specific melting temperature, especially specific hydrophobic-lipophobic balance (HLB)) in specific adjuvant chips, flakes or granules or powders (i.e., containing greater than or equal to 5% hydrophobic emollient oils and/or humectants in the adjuvant chips, the polyol ester to oil/humectant ratio greater or equal to 1:1, and the polyol ester to other structurant ratio greater than 1:1) will result in bars, processed by adjuvant technology, with enhanced oil/humectant carrying and releasing capabilities. These capabilities are crucial to benefit delivery to the skin via personal wash.

Not to be bound by the theory, it is believed that the adjuvant chips of the subject invention entrapped emollient oils by a mechanism that is different from those of prior art. That is, hydrophobic oils such as sunflower seed oil tend to be miscible with said polyol esters during mixing (temperature between 65–120° C.) to form an one phase isotropic liquid. Upon cooling, the oil may not be in the form of discrete droplets as is found in the adjuvant chips where polyalkylene glycol is the major carrier. Instead, oils may exist in the crystalline cracks or even in the form of solid solution in the chips of the subject invention. The chemical affinity of oil and polyol ester is believed to contribute significantly to the stability of the oils in the polyol ester carrier.

BRIEF SUMMARY OF THE INVENTION

In one embodiment of the invention, applicants have unexpectedly found that, when specific additive compositions are made containing a specific polyol ester with defined HLB as the major carrier for liquid hydrophobic emollient oil and/or liquid hydrophilic humectant, oil carrying and releasing capabilities can be simultaneously improved.

Specifically, in this embodiment the invention comprises an adjuvant composition in the forms of chips, powders, granules or mixtures thereof comprising (% by wt.):

(a) a carrier comprising
(1) 50% to 95%, preferably 65% to 90% of total chip composition a solid, amphiphilic polyol ester having the following structure described as

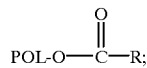

wherein POL represents the polyol moiety, R represents an organic hydrophobic group, and one or more R—(C=O)—O— functional groups are chemically attached to one or more hydroxy groups of the polyol moiety;

said solid, amphiphilic polyol ester having a hydrophilic-lipophilic balance (HLB) number at between 2.5 and 15, preferably between 3 and 8; said polyol ester having melting temperature at between 40° C. and 90° C., preferably at between 45° C. and 70° C.;

said solid, amphiphilic polyol ester includes but not being limited to glycerin fatty esters, such as glyceryl monolaurate and glyceryl monostearate; alkylene glycol fatty esters, such as ethylene glycol monostearate and ethylene glycol monolaurate; pentaeryrthrityl fatty esters such as pentaeryrthrityl stearate; polyglycerin fatty esters such as hexaglyceryl tristearate; and (2) 0 to 50%, preferably 0 to 30% of total chip composition of an optional carrier selected from the group consisting of polyalkylene glycol having molecular weight of about 4000–25000, paraffin, C8–C22 carboxylic acid, C8–C22 alcohol, water soluble starches and mixtures thereof;

wherein the total weight percentage of the said optional carrier (2) being less than the total weight percentage of the said polyol ester described in (1). This specification on the upper limit of the optional structurants is a criticality because above this range, the bar has its oil structuring capability reduced, which causes oil leakage and/or oil phase separation from the bulk (see Example 1); or the bar has its oil releasing capability reduced, which prevents the oil release into the aqueous washing liquor and deliver to the skin via the personal washing route (see Example 1); and (b) 5% to 50%, preferably 10% to 35%, most preferably 10% to 25% chip composition of a liquid hydrophobic emollient oil, liquid hydrophilic humectant or a mixture thereof;

the weight ratio of said polyol ester as carrier (1) in (a) to the sum of said emollient oil and/or humectants (b) being greater than or equal to 1:1, preferably greater than or equal to 1.5:1; this carrier to emollient ratio is a criticality because below this ratio, oil and humectant tend to separate from the bulk of the solid matrix.

In another embodiment, the invention comprises an extruded bar composition which is produced using about 5 to 80%, preferably 10 to 50%, most preferably 20% to 40% said adjuvant compositions in the form of solid chips, flakes, powders, granules or mixtures thereof; and about 20 to 95% of a surfactant system (base) in the form of chips, flakes, granules or mixtures thereof, wherein the surfactant is selected from the group consisting of anionic surfactants, amphoteric surfactants, nonionic surfactants, cationic surfactants and mixtures thereof. The surfactant system may also contain minor amounts of fragrances, preservative, skin feel modifier (e.g., guar) etc. It may also contain free fatty acid and/or structurant/inert filler.

The surfactant system of the second chip preferably comprises either or both of the following ingredients:

(i) carboxylic acid soap;

(ii) synthetic anionic surfactant, preferably in the solid form at 25° C., such as sodium cocoyl isethionate, and an amphoteric surfactant such as cocoamidopropyl betaine.

In the third embodiment of the invention, the invention comprises a method of making benefit agent containing adjuvant compositions in the form of chips, flakes, granules, powders or mixtures thereof comprising:

(1) 50–95% of a carrier selected from group (a) (1)-(2) above;

(2) 5 to 50% benefit agents selected from group (b);

(3) 0–10% optional ingredients selected from thickeners and rheology modifiers;

(4) 0–10% water.

BRIEF DESCRIPTION OF THE DRAWINGS

FIG. 1 presents the phase diagram of PEG 8000, fatty (stearic/palmitic) acid and polyol ester (glyceryl monolaurate) at 95° C. The ternary system contains sunflower seed oil at fixed level of 20% wt (i.e., the total concentration of PEG 8000, fatty acid and the glyceryl monolaurate equals to 80% total composition).

DETAILED DESCRIPTION OF THE INVENTION

The present invention relates to novel personal washing bar compositions comprised of (1) adjuvant chips containing skin benefit agents and (2) base chips containing a surfactant system.

Particularly, said adjuvant chips are made containing a specific polyol ester with defined HLB and defined melting temperature as the major carrier for liquid hydrophobic oils and/or hydrophilic humectants. Unexpectedly, applicants have found that when the HLB of the solid polyol ester is between 2.5 and 15, preferably between 3 and 8, high levels of the emollient oil and the humectant can be satisfactorily structured in the solid matrix, and the solid matrix permits oil and humectant to be release to aqueous washing liquid to be delivered to the skin via personal wash.

The invention further comprises an extruded bar composition which is produced using about 5 to 80%, preferably 10 to 50%, most preferably 20% to 40% said adjuvant compositions in the form of solid chips, flakes, powders, granules or mixtures thereof; and about 20 to 95% of a surfactant system (base chips) in the form of chips, flakes, granules or mixtures thereof, wherein the surfactant is selected from the group consisting of anionic surfactants, amphoteric surfactants, nonionic surfactants, cationic surfactants and mixtures thereof. The surfactant system may also contain minor amounts of fragrances, preservative, skin feel modifier (e.g., guar) etc. It may also contain free fatty acid and/or structurant/inert filler.

The surfactant system of the second chip preferably comprises either or both of the following ingredients:

(i) carboxylic acid soap;

(ii) synthetic anionic surfactant, preferably in the solid form at 25° C., such as sodium cocoyl isethionate, and an amphoteric surfactant such as cocoamidopropyl betaine.

In another embodiment of the invention, the invention comprises a method of making benefit agent containing adjuvant compositions in the form of chips, flakes, granules, powders or mixtures thereof comprising:

(1) 50–95% of a carrier selected from group (a) (1)-(2) above;

(2) 5 to 50% benefit agents selected from group (b);

(3) 0–10% optional ingredients selected from thickeners and rheology modifiers;

(4) 0–10% water.

(a) Adjuvant Chips (1) Carrier

A solid, amphiphilic, polyol ester comprises 50% to 95%, preferably 65% to 90%, of total composition of the adjuvant chip composition.

Said amphiphilic polyol ester is specified by its hydrophilic lipophilic balance (HLB) value that is defined by Becher and Schick and by Marszall in Chapter 8 and Chapter 9 of *Nonionic Surfactants—Phase Chemistry*, Surfactant Sci. Series, Vol. 23, P439–549, which is hereby incorporated by reference into the subject application. Said solid, amphiphilic polyol ester has a hydrophilic-lipophilic balance (HLB) value between 2 and 15, preferably between 2.5 and 10, and most preferably between 3 and 8. The HLB range of the polyol ester is a criticality because below the range, the polyol ester can bind too tightly with the oil (b) and not allow the oil to be released to the aqueous solution, which prevents the oil to be delivered to the skin; and above the HLB range, the polyol ester does not have the capability to structure the emollient oil and the humectant described in (b) in the solid bar matrix and causes oil leakage and separation from the bulk.

Said polyol ester has a melting temperature between 40° C. and 90° C., preferably at between 45° C. and 70° C.; such that the matrix formed by the polyol ester to trap the oil is in the solid form in the bar under in-use condition.

The weight ratio of the said polyol ester to the sum of the emollient oil and the humectants, both described in (b), is greater than or equal to 1:1, preferably greater than or equal to 1.5:1; this weight ratio is a criticality because below this ratio, the oil and the humectant can not be satisfactorily contained in the solid matrix of the bar, which leads to oil leakage and separation from the bulk.

The said solid, amphiphilic polyol ester is defined as a polyol esterified or partially esterified by an organic acid that can be represented by

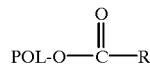

in which POL is a polyol moiety, R is a hydrophobic moiety, and one or more {—O—(C=O)—R} functional groups are chemically attached to one or more hydroxy groups of the polyol moiety.

For example, the polyol moiety (POL) may be derived from glycerol, glycerin, propylene glycol, polypropylene glycols, ethylene glycol, polyethylene glycols, ethyl hexanediol, hexylene glycols and pentaeryrthrityl or mixtures thereof.

The hydrophobic group R is selected from the derivatives of alkyl, aryl, alkylaryl, alkylene, acyl, and fat and oil derivatives or mixtures thereof. Preferably R is the derivative of a C8–C22 straight or branched chain alkyl functioning group, most preferably a C12–C22 alkyl functioning group.

Examples of said solid, amphiphilic polyol ester include glycerin fatty esters and glycerol esters, such as glyceryl monolaurate (from Henkel under the tradename of Monomuls 90L-12) and glyceryl monostearate (from Stepan under the tradename of GMS Pure); alkylene glycol fatty esters, such as ethylene glycol monostearate and ethylene glycol monolaurate (from RP under the tradename of Alkamuls); pentaeryrthrityl fatty esters such as pentaeryrthrityl stearate; polyglycerin fatty esters such as hexaglyceryl tristearate. The physical properties of a few suitable polyol esters were listed in Table 1.

TABLE 1

Examples and properties of the suitable polyol esters for the subject invention

| Polyol Ester | Melting temperature (°C.) | HLB Value | Tradename/ supplier |
|---|---|---|---|
| Glyceryl monolaurate | 56–65 | 4.9 | Monomuls 90L-12/ Henkel Corp. |
| Glyceryl monostearate | 56–65 | 3.8 | Kessco GMS Pure lStepan |
| Ethylene glycol stearate | 52–56 | 2.9 | Kessco EGMS 70/ Stepan |

The adjuvant chip compositions may also contain an optional structurant and/or filler. Such structurants can be used to improve the processing properties, and enhance desired user sensory profiles, and modify the dissolution rates of the adjuvant chips to enhance bar's integrity.

The total weight percentage of said optional structurant and/or filler has to be less than the weight percentage of the said polyol ester in the adjuvant chip composition. This specification on the upper limit of the optional structurants is a criticality because above this range, the chip composition has its oil structuring capability reduced, which causes oil leakage and/or oil phase separation from the bulk; or the bar has its oil releasing capability reduced, which prevents the oil release into the aqueous washing liquor and deliver to the skin via the personal washing route.

Said optional structurant is generally long chain, preferably straight and saturated, (C$_8$–C$_{24}$) fatty acid or ester derivative thereof; and/or branched long chain, preferably straight and saturated, (C$_8$–C$_{24}$) alcohol or ether derivatives thereof.

The optional structurant can also be polyalkylene glycol with molecular weight between 2000 and 20,000, preferably between 3000 and 10,000. Those PEGs are commercially available, such as those marketed under the tradename of CARBOWAX SENTRY PEG 8000 or PEG 4000 by Union Carbide.

The optional structurants that can be used include starches, preferably water soluble starches such as maltodextrin and polyethylene wax or paraffin wax.

The optional structurant can also be selected from water soluble polymers chemically modified with hydrophobic moiety or moieties, for example, EO-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm® (PEG modified glyceryl cocoate, palmate or tallowate) from Rewo Chemicals.

The optional structurants also include Amerchol Polymer HM 1500 (Nonoxynyl Hydroethyl Cellulose).

(2) Skin Benefit Agents

The adjuvant chips contain 5% to 50%, preferably 10% to 35%, most preferably 10% to 25% total bar composition a liquid hydrophobic emollient oil, a liquid hydrophilic humectant or mixtures thereof.

Said liquid hydrophobic emollient oil has a solubility of less than 10%, preferably less than 5%, and most preferably less than 1% in water at 25° C.

Said liquid emollient oil has a melting temperature of less than 25° C. and has a viscosity less than $10^5$ centipoise, preferably less than 50,000 centipoise, most preferably less than 10,000 centipoise at 25° C. The defined melting temperature and viscosity range of said oil is a criticality since keeping the oil in a free flow liquid state is important for satisfactory bar mixing as well as for pouring into the bar mold when preferred cast melt process is applied. For example, above the viscosity range, oil becomes very thick, and this prevents the efficiently mixing of the bar ingredients at molten state (e.g., 85–125° C.), reduces the pourability of the melt, and causes bar in homogeneity and processing difficulties.

The emollient oil is selected from the group consisting of hydrocarbon oils, silicones, liquid diglycerides, liquid triglycerides, liquid di- and tri-glyceride derivatives, liquid hydrocarbon esters, silicones, sterols, lanolins and sunscreen oils.

Examples of hydrocarbon oils are mineral oil, petrolatum, C8–C24 straight or branched chain alkyl or alkenyl compounds.

Examples of liquid di- and tri-glycerides and their derivatives are sorbitol, coconut oil, jojoba oil, maleated soybean oil, castor oil, almond oil, peanut oil, wheat germ oil, rice bran oil, linseed oil, apricot pits oil, walnuts, palm nuts, pistachio nuts, sesame seeds, rape seed oil, cade oil, corn oil, peach pit oil, poppyseed oil, pine oil, soybean oil, avocado oil, sunflower seed oil, hazelnut oil, olive oil, grapeseed oil, and safflower oil, Shea butter, babassu oil, milk glycerides and mixtures thereof.

Examples of silicone oil include dimethicone copolyol, and dimethylpolysiloxane.

Examples of hydrocarbon esters include isopropyl myristate and isocetyl palmitate.

Examples of the sunscreen oils include UV-absorbing oils selected from the group consisting of butyl methoxydibenzoylmethane (tradename: Parsol 1789), PABA, octyl methoxy cinnamate (tradename: Parsol MCX), benzophenone quat, niacinamide, padimate 0, P-proline.

It is more preferred that the emollient oil is selected from liquid di- and tri-glycerides and their derivatives.

The liquid hydrophilic humectant, when used, has a solubility of greater than or equal to 50% wt. in water at 25° C.

Said liquid humectant has a melting temperature at less than 25° C. and has a viscosity at less than 5000 centipoise, preferably less than 1000 centipoise.

The humectant is selected from polyols consisting of glycerol, glycerin, propylene glycol, liquid polyalkylene glycols such as polypropylene glycols, polyethylene glycols with molecular weight less than 1000 (such that they are in liquid state at 25° C.), ethyl hexanediol, and hexylene glycols.

(3) Other Ingredients

In addition, the adjuvant chip composition of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The chip composition may further comprise antimicrobials such as 2-hydroxy-4,2'4' trichlorodiphenylether (DP300); preservatives such as dimethyloldimethylhydantoin (Glydant XL 1000), parabens, sorbic acid etc.

The chip composition may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers as conditioners which may be used include Quatrisoft LM-200 Polyquaternium-24, Merquat Plus 3330-Polyquaternium 39; and Jaguar® type conditioners.

The chip composition may also comprise 0–10% of the total chip composition a thickening agent selected from silicas, starches or mixture of both. Preferably, said starches are maltodextrin or potato or corn starch. A referred silica is fumed silica, generally produced by the hydrolysis of silicon tetrachloride vapor in a flame of hydrogen and oxygen. The process produces particles of from 7 to 30 millimicrons. Preferably, said thickeners are incorporated in the chip under the condition that said optional structurants (defined in (1)) are included in the chip composition.

(b) Base Chips (1) Surfactant System

The base chip composition of the subject invention generally comprises 10% to 70%, preferably 15% to 60%, and most preferably 25 to 50% total chip composition surfactant or mixtures of surfactants. The surfactants generally comprise anionic surfactants, amphoteric surfactants, nonionic surfactants, cationic surfactants and mixtures thereof, preferably anionic surfactants, amphoteric surfactants, nonionic surfactants and mixtures thereof.

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

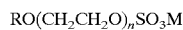

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation; amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

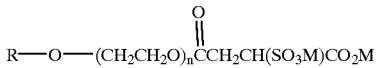

wherein n=1 to 20; and M is as defined above.

Sarcosinates are generally indicated by the formula $$RCON(CH_3)CH_2CO_2M,$$

wherein R ranges from $C_8$–$C_{20}$ alkyl and M is a solubilizing cation.

Taurates are generally identified by formula $$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R\text{—}(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Iiardi et al., U.S. Pat. No. 5,393,466, hereby incorporated by reference into the subject application. This compound has the general formula:

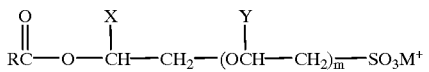

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Said anionic surfactants include C8–C24 carboxylate fatty acid soap can also be used as the major anionic surfactants for the bar composition.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

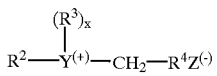

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl) ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

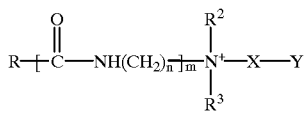

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric detergents within the above general formula include simple betaines of formula:

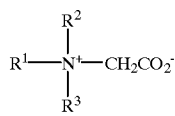

and amido betaines of formula:

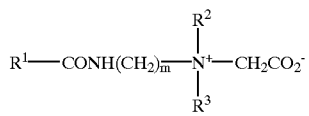

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

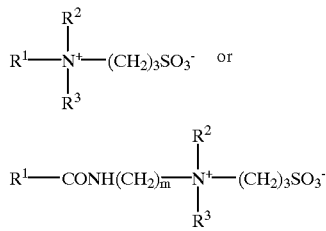

where m is 2 or 3, variants of these in which —$(CH_2)_3SO^-_3$ is replaced by

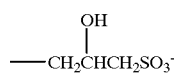

In these formulae $R^1$, $R^2$ and $R^3$ are as discussed previously.

A further possibility is that the amphoteric detergent is a sulphobetaine of formula

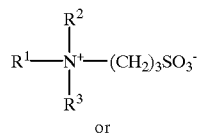

or

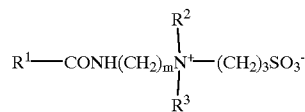

where m is 2 or 3, or variants of these in which —$(CH_2)_3 SO_3^-$ is replaced by

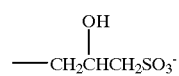

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic generally comprises 0.1 to 20% by weight, preferably 0.1% to 15%, more preferably 0.1 to 10% by wt. of the composition.

In addition to one or more anionic and amphoteric and/or zwitterionic, the surfactant system may optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

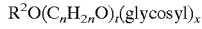

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

(2) Optional Ingredients

The base chip compositions may also comprise an optional structurant and/or filler. Such structurants can be used to improve the processing properties, and enhance desired user sensory profiles, and modify the melting temperature, Krafft temperature, and dissolution rates of the base chips to enhance bar's integrity.

Said optional structurant is generally long chain, preferably straight and saturated, ($C_8$–$C_{24}$) fatty acid or ester derivative thereof; and/or branched long chain, preferably straight and saturated, ($C_8$–$C_{24}$) alcohol or ether derivatives thereof.

The optional structurant can also be polyalkylene glycol with molecular weight between 2000 and 20,000, preferably between 3000 and 10,000. Those PEGs are commercially available, such as those marketed under the tradename of CARBOWAX SENTRY PEG 8000 or PEG 4000 by Union Carbide.

The optional structurants that can be used include starches, preferably water soluble starches such as maltodextrin and polyethylene wax or paraffin wax.

The optional structurant can also be selected from water soluble polymers chemically modified with hydrophobic moiety or moieties, for example, EO-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm® (PEG modified glyceryl cocoate, palmate or tallowate) from Rewo Chemicals.

The optional structurants also include Amerchol Polymer HM 1500 (Nonoxynyl Hydroethyl Cellulose).

In addition, the base chip composition of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The chip composition may further comprise antimicrobials such as 2-hydroxy-4,2'4' trichlorodiphenylether (DP300); preservatives such as dimethyloldimethylhydantoin (Glydant XL1000), parabens, sorbic acid etc.

The chip composition may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers as conditioners which may be used include Quatrisoft LM-200 Polyquaternium-24, Merquat Plus 3330—Polyquaternium 39; and Jaguar® type conditioners.

Polyethylene glycols as conditioners which may be used include:

| | | |
|---|---|---|
| Polyox | WSR-205 | PEG 14M, |
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

The present invention is set forth in greater detail in the examples which follow. The examples are for illustration purposes only and are not intended to limit the scope of the claims in any way.

All percentages in the examples and specification, unless indicated otherwise, are intended to be percentages by weight.

EXAMPLE 1

Advantages of Using Polyol Ester as Oil Structurant in Comparison with PEG 8000 and Palmitic/stearic Acid Carrying 20% sunflower seed oil, a bar structuring system comprised of Polyol ester (glyceryl monolaurate), PEG 8000 and fatty acid was selected to test the formulation space for satisfactory oil structuring and releasing capabilities.

Comparative 1

Shown in the ternary phase diagram (FIG. 1), samples containing high levels of PEG 8000 (i.e., concentration of PEG 8000 is above 50% total structuring system) separated into an oily top layer and a bottom layer comprised of the rest. Cooling the PEG-rich samples to room temperature resulted in tacky solids with oil leaking out. This implies that PEG 8000 is not suitable as the major structurant for a high oil bar, which is consistent with the findings discussed in Example 2.

Comparative 2

In the fatty acid rich region of the FIG. 1 (i.e., concentration of FA is above 60% total structuring system), samples formed single isotropic liquids at 95° C. Cooling those samples to 25° C. resulted in firm, crisp solids. However, there was no oil released from the solids into water, as observed under optical microscopy, and this was not desired for benefit delivery. Thus the traditional hydrophobic binders, such as stearic/palmitic acid or wax are not ideal as the major structurants for the high oil bars.

Invention

In the polyol ester rich region (i.e., glyceryl monolaurate concentration is above 50%), samples formed single-phase isotropic liquids at 95° C. Cooling the molten mixtures to 25° C. resulted in firm, crisp solids, which permitted oil release into aqueous phase. Thus monoglyceride should be used as the major structurant (i.e., 50% and above of the total bar structuring system) for the optimum oil-carrying and releasing.

EXAMPLE 2

Preparation of Oil-Containing Adjuvant Chips

Adjuvant Chips were prepared by first melting 1500 grams of glycerol monostearate (from Stepan, under tradename of GMS pure) at temperatures between 85° C. and 120° C. using an overhead mixer for 30–120 minutes and allowing the GMS to deaerate. Then sunflower seed oil were stirred in. Upon melting and homogenous mixing, glycerol monostearate and sunflower seed oil became miscible with each other and formed an isotropic solution. Then the isotropic solution was gradually poured onto a chill roll with temperatures set between 0 to 15° C. and collected as adjuvant chips or flakes. The adjuvant chips contain 30% sunflower seed oil and 70% glycerol monostearate and have melting temperatures between 50 and 70° C.

EXAMPLE 3

Preparation of a Finished Bar Containing Dove®

857 grams of the adjuvant chips (containing 30% sunflower seed oil) prepared by Example 1 were combined with 2000 grams of Dove® as base chips containing a surfactant system (representing 70% of final bar) in a Ribbon blender were plodded under vacuum in a Weber Seelander duplex refiner with screw speed at about 20 rpm. The nose cone of the plodder was heated to 45–50° C. The cut billets were stamped into bars using a Weber Seelander L4 hydraulic press with a nylon, pillow-shaped die in place.

The Finished bar contains 70% Dove® as the base chips and 30% said adjuvant chips. Said Dove(R) base chips have the following composition:

about 40–60% fatty acid isethionate;

about 20–30% fatty acid;

about 1–10% sodium isethionate;

about 5% cocoamidopropyl betain; and remainder preservative, dyes, water, and other minors.

Plodding throughput rate was as good as Dove® alone. The experiments show that the emollient containing chips can be successfully incorporated into bars without affecting the processing, and thus the emollients (in this case, sunflower seed oil can be subsequently delivered. The bar also provided interesting sensory cues including creamy, dense lather, and oily moisturized skin after-wash.

EXAMPLE 4

Preparation of a Finished Bar Containing 82/18 Fatty Acid Soap

30% adjuvant chips, containing 30% sunflower seed oil, prepared by Example 1 were combined with 82/18 fatty acid soap as base chips, representing 70% of the final bar. The 82/18 fatty acid soap was first heated in a sigma blade mixer until the material became soft and pliable. The moisture was adjusted so as to have the final product containing 10%–13% moisture. At this time perfume was also added so as to have the final product containing 1.5% perfume. Then the fatty acid soap chips were refined into 3 mm diameter pellets and mixed in a bowl with the adjuvant chips. The blend was then re-refined into 3 mm diameter pellets to insure homogeneity of the 82/18 soap and the adjuvant chips. Further processing produced extruded billets which were cut and stamped into bars. No point of the process was hindered by the addition of adjuvant chips to the soap base.

We claim:

1. An extruded toilet bar composition comprising 5% to 80% of base chips containing a surfactant system and 5% to 80% adjuvant chips comprising:

(A) 50% to 95% of the chip composition of a carrier comprising a solid, amphiphilic polyol ester having the following structure:

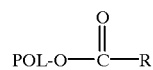

wherein POL represents polyol moiety, R represents an organic hydrophobic group, and one or more —O—(C=O)—R functional groups are chemically attached to one or more hydroxy groups in the polyol moiety to achieve partial or total esterification;

said solid, amphiphilic polyol ester having a hydrophilic-lipophilic balance (HLB) number at between 2 and 15, said polyol ester having melting temperature at between 40° C. and 90° C.; and (B) 5% to 50% a liquid hydrophobic emollient oil or a liquid humectant or mixtures thereof;

the weight ratio of said polyol ester (A) to the sum of said emollient oil and/or humectant (B) being greater than or equal to 1:1;

said liquid hydrophobic emollient oil having a water solubility less than 10% in water at 25° C.; said liquid emollient oil having a melting temperature of less than 25° C.; said oil having a viscosity less than $10^5$ centipoise at 25° C.;

and wherein said emollient oil is selected from the group consisting of C8–C24 hydrocarbon oils, silicones, liquid diglycerides, liquid triglycerides, liquid di- and tri-glyceride derivatives, vegetable oils, vegetable oil derivatives, sterols, lanolins and mixtures thereof;

said liquid hydrophilic humectant having a solubility of greater than or equal to 50% wt. in water at 25° C.; said liquid humectant having a melting temperature at less than 25° C. and having a viscosity of less than 5000 centipoise at 25° C.;

and wherein said humectant is selected from polyols consisting of glycerol, glycerin, C1–C10 alkylene glycols such as propylene glycol, liquid polyalkylene glycols such as polypropylene glycols, polyethylene glycols with molecular weight less than 1000, ethyl hexanediol, and hexylene glycols.

2. A composition according to claim 1, wherein the polyol ester or mixtures of the polyol ester comprise 65% to 90% of total adjuvant chip composition.

3. A composition according to claim 1, wherein the hydrophobic emollient oil and/or the liquid humectant or the mixtures thereof comprise of 10% to 35% total adjuvant chip composition.

4. A composition according to claim 1, wherein the hydrophobic emollient oil and/or the liquid humectant or the mixtures thereof comprise of 10% to 25% total adjuvant chip composition.

5. A composition according to claim 1, wherein the polyol ester has a melting temperature of between 45° C. and 70° C.

6. A composition according to claim 1, wherein the polyol ester has a HLB value between 2.5 and 10.

7. A composition according to claim 1, wherein the polyol ester has a HLB value between 3 and 8.

8. A composition according to claim 1, wherein the weight ratio of said polyol ester to the sum of the emollient oil and humectant is greater or equal to 1.5:1.

9. A composition according to claim 1, wherein the weight ratio of said polyol ester to the sum of the emollient oil and humectant is greater or equal to 2:1.

10. A composition according to claim 1, wherein the solid, amphiphilic polyol ester is selected from the group consisting of glycerin fatty esters, alkylene glycol fatty esters, pentaerythrityl fatty esters, polyglycerin fatty esters, and mixtures thereof.

11. A composition according to claim 10, wherein the glycerin fatty ester is glyceryl monostearate or glyceryl monolaurate.

12. A composition according to claim 10, wherein the alkylene glycol fatty ester is ethylene glycol monostearate or ethylene glycol monolaurate.

13. A composition according to claim 10, wherein the pentaerythrityl fatty ester is pentaerythrityl monostearate or pentaerythrityl monolaurate.

14. A composition according to claim 1, wherein the humectant has a viscosity less than 1000 centipoise at 25° C.

15. A composition according to claim 1, wherein the hydrophobic emollient oil has a viscosity less than 5000 centipoise at 25° C.

16. A composition according to claim 1, wherein the hydrophobic emollient oil has a viscosity less than 1000 centipoise at 25° C.

17. A composition according to claim 1, wherein the hydrophobic emollient oil has a solubility less than 5% wt. in water at 25° C.

18. A composition according to claim 1, wherein the hydrophobic emollient oil has a solubility less than 1% wt. in water at 25° C.

19. A composition according to claim 1, further comprising 0 to 50% total chip composition of an optional structurant, and the total weight percentage of said optional structurant is less than the total weight percentage of said polyol ester described in claim 1; and said optional structurant is a solid selected from $C_8$–$C_{24}$ straight and saturated fatty acid or ester derivative thereof; and/or $C_8$–$C_{24}$ straight and saturated, alcohol or ether derivatives thereof; polyalkylene glycol with molecular weight between 2000 and 20,000; starches; water soluble polymers chemically modified with hydrophobic moiety or moieties, and mixtures thereof.

20. A composition according to claim 19, wherein the optional structurant comprises 5% to 30% total adjuvant chip composition.

21. A composition according to claim 1, further comprising 0 to 10% total adjuvant chip composition of an optional thickener.

22. A composition according to claim 21, wherein the optional thickener is selected from silicas and starches.

23. A composition according to claim 22, wherein said silica is fumed silica.

24. A composition according to claim 22, wherein the starches are selected from maltodextrin, corn starch, and potato starch.

25. A composition according to claim 1, further comprises 0–10% water.

26. A composition according to claim 1, wherein said adjuvant chips are in the physical forms selected from powder, noodle, particle, and granule.

27. A composition according to claim 1, wherein said base chips comprise a lathering surfactant selected from the group consisting of anionic surfactants nonionic surfactants, cationic surfactants, amphoteric surfactants and mixtures thereof.

28. A composition according to claim 27, wherein the anionic surfactant is sodium acyl isethionate.

29. A composition according to claim 27, wherein the anionic surfactant is a salt of a carboxylic acid.

30. A composition according to claim 27, wherein the amphoteric surfactant is cocoamidopropyl betaine.

31. A composition according to claim 1, further comprising 0–10% water.

32. A composition according to claim 1, further comprising 0 to 70% an optional structurant selected from $C_8$–$C_{24}$ straight and saturated fatty acid or ester derivative thereof; and/or $C_8$–$C_{24}$ straight and saturated, alcohol or ether derivatives thereof; polyalkylene glycol with molecular weight between 2000 and 20,000; starches; water soluble polymers chemically modified with hydrophobic moiety or moieties, and mixtures thereof.

33. A composition according to claim 1, further comprises 0–10% minor ingredients selected from fragrances, preservatives, cationic polymers, antioxidants, and titanium oxide.

34. A composition according to claim 1, wherein the hydrophobic liquid emollient oil is a UV-absorbing, sun protecting oil.

\* \* \* \* \*